(12) United States Patent
Mogaka

(10) Patent No.: US 9,205,024 B1
(45) Date of Patent: Dec. 8, 2015

(54) INTRAVENOUS MEDICATION DELIVERY SAFETY ASSEMBLY

(76) Inventor: Joram O. Mogaka, Farmington Hills, MI (US)

(*) Notice: Subject to any disclaimer, the term of this patent is extended or adjusted under 35 U.S.C. 154(b) by 1085 days.

(21) Appl. No.: 13/241,630

(22) Filed: Sep. 23, 2011

(51) Int. Cl.
A61J 1/10 (2006.01)
A61J 1/14 (2006.01)
A61J 1/05 (2006.01)

(52) U.S. Cl.
CPC .... *A61J 1/10* (2013.01); *A61J 1/05* (2013.01); *A61J 1/1475* (2013.01); *A61M 2205/50* (2013.01); *A61M 2205/60* (2013.01)

(58) Field of Classification Search
CPC ............ A61M 37/00; A61M 2205/50; A61M 2205/60; A61M 5/14244; A61M 5/148; A61J 1/10; A61J 1/14; A61J 1/1412; A61J 1/1462; A61J 1/1475; A61J 1/1481; A61J 2200/76; A61J 1/05; A61J 2200/70; A61J 2205/60
USPC ........................... 604/257, 258, 260, 262, 408
See application file for complete search history.

(56) References Cited

U.S. PATENT DOCUMENTS

| | | | |
|---|---|---|---|
| 5,651,775 A | 7/1997 | Walker et al. | |
| 6,641,562 B1 * | 11/2003 | Peterson | 604/141 |
| D490,112 S | 5/2004 | Hadzic et al. | |
| 7,588,189 B2 | 9/2009 | Fago et al. | |
| 7,704,231 B2 | 4/2010 | Pongpairochana et al. | |
| 2006/0265246 A1 | 11/2006 | Hoag | |
| 2007/0208308 A1 | 9/2007 | Gibson et al. | |
| 2010/0249728 A1 * | 9/2010 | Kobashi et al. | 604/262 |

* cited by examiner

Primary Examiner — Imani Hayman

(57) ABSTRACT

An intravenous medication delivery safety assembly insures proper medication is delivered to a patient. The assembly includes an IV bag holding a medication. A tube has a first end coupled to the bag. A microchip is coupled to the tube proximate a second end of the tube. The microchip provides identifying data corresponding to the medication in the bag. A conduit is selectively coupled to the second end of the tube. The conduit is configured for coupling to a cannula. A security mechanism is coupled to the conduit to prevent coupling the tube to the conduit. A processor is coupled to the conduit and includes confirmation data corresponding to the patient to receive the medication. The processor reads the microchip and is operationally coupled to the security mechanism to permit coupling of the tube to the conduit only when the confirmation data properly corresponds to the identifying data.

10 Claims, 6 Drawing Sheets

INTRAVENOUS MEDICATION DELIVERY SAFETY ASSEMBLY

BACKGROUND OF THE DISCLOSURE

Field of the Disclosure

The disclosure relates to medication delivery devices and more particularly pertains to a new medication delivery device for insuring proper medication is delivered to a patient.

SUMMARY OF THE DISCLOSURE

An embodiment of the disclosure meets the needs presented above by generally comprising an IV bag holding a medication. A tube has a first end coupled to the bag. A microchip is coupled to the tube proximate a second end of the tube. The microchip provides identifying data corresponding to the medication in the bag. A conduit is selectively coupled to the second end of the tube. The conduit is configured for coupling to a cannula. A security mechanism is coupled to the conduit to prevent coupling the tube to the conduit. A processor is coupled to the conduit and includes confirmation data corresponding to the patient to receive the medication. The processor reads the microchip and is operationally coupled to the security mechanism to permit coupling of the tube to the conduit only when the confirmation data properly corresponds to the identifying data.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
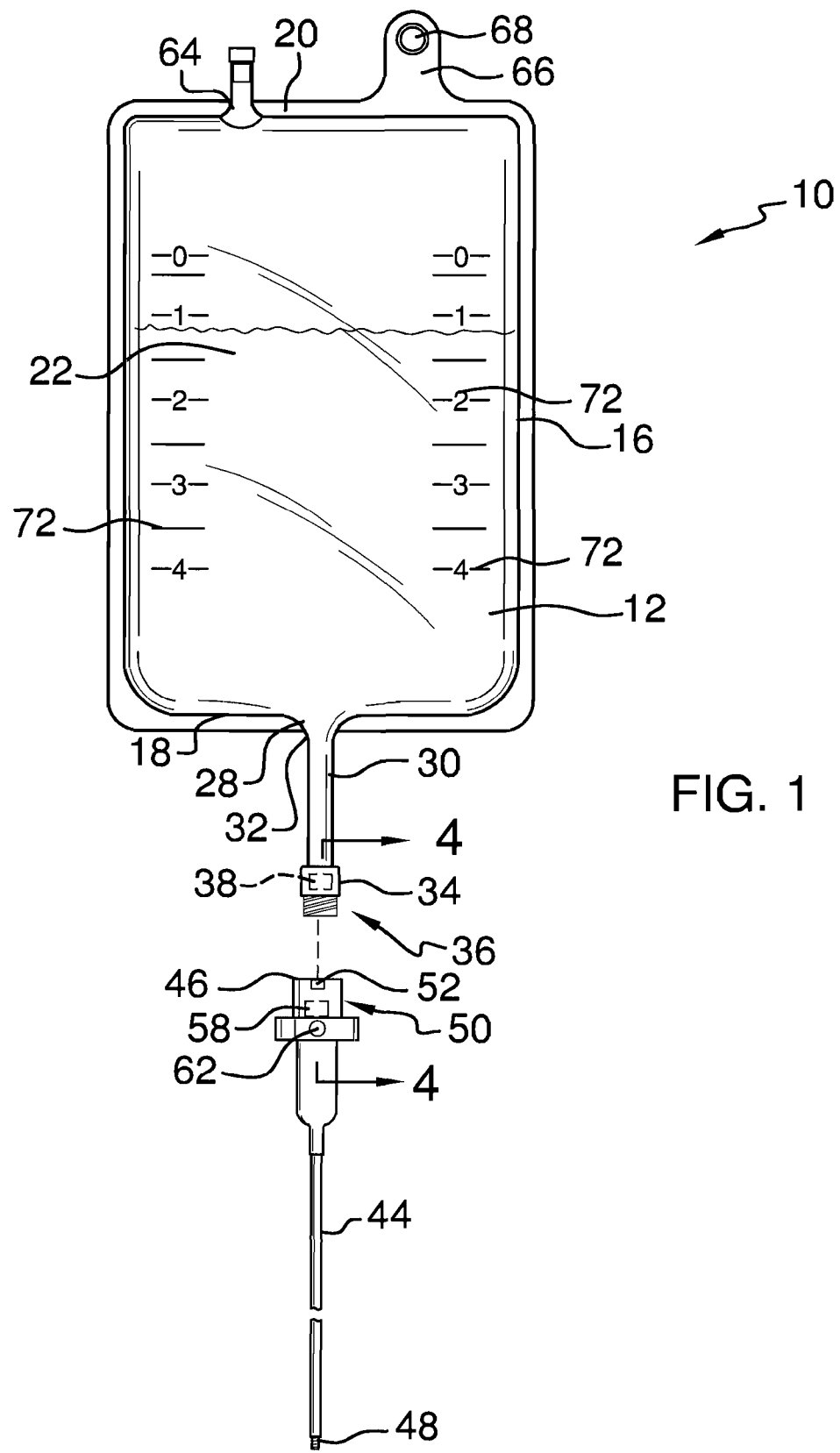
FIG. 1 is a partially exploded front view of an intravenous medication delivery safety assembly according to an embodiment of the disclosure.
Figure 2:
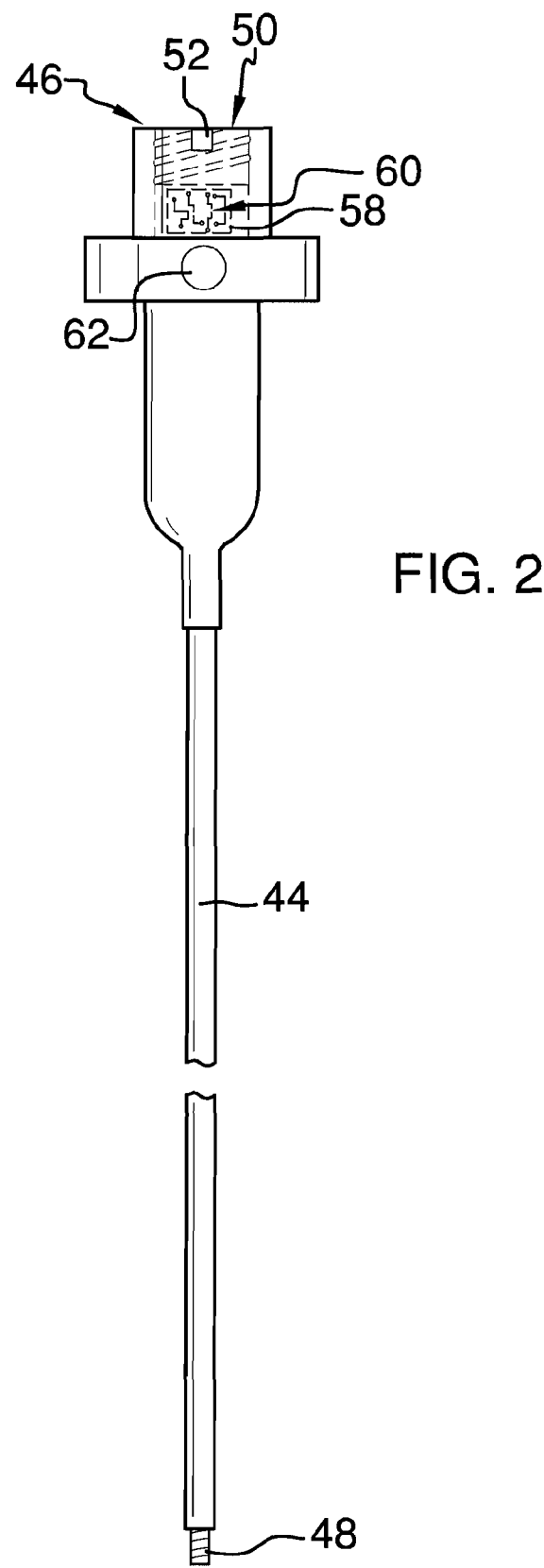
FIG. 2 is a front view of an embodiment of the disclosure.
Figure 3:
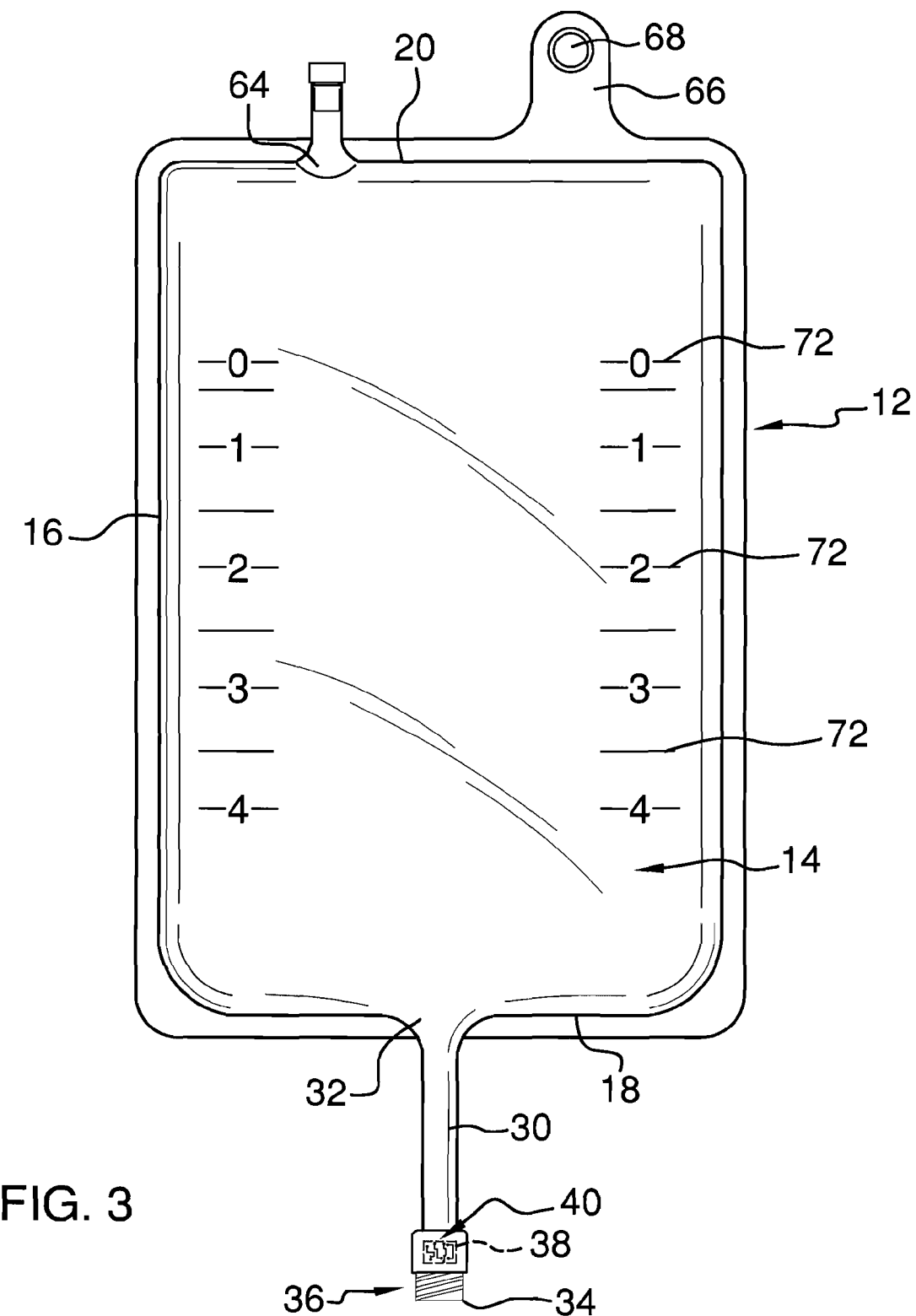
FIG. 3 is a front view of an embodiment of the disclosure.
Figure 4:
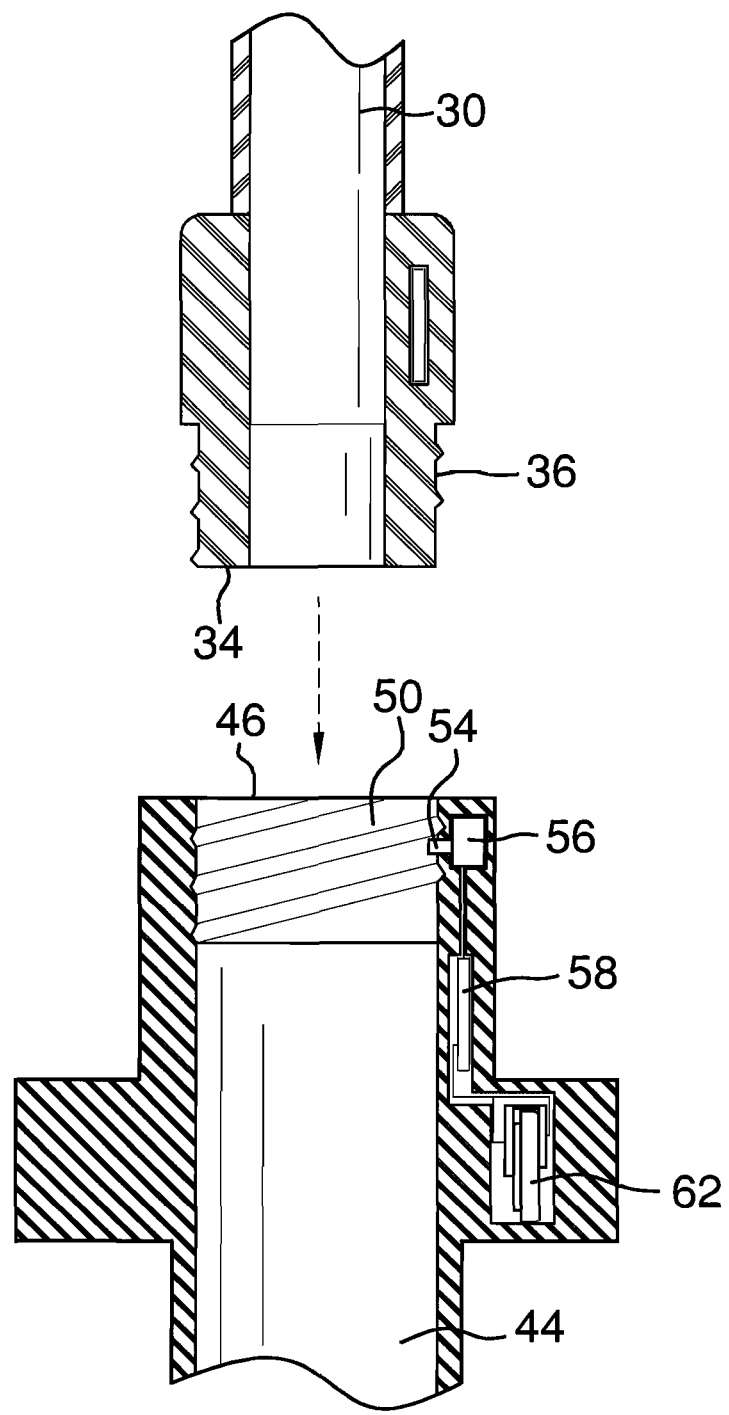
FIG. 4 is a cross-sectional view of an embodiment of the disclosure taken along line 4-4 of FIG. 1.
Figure 6:
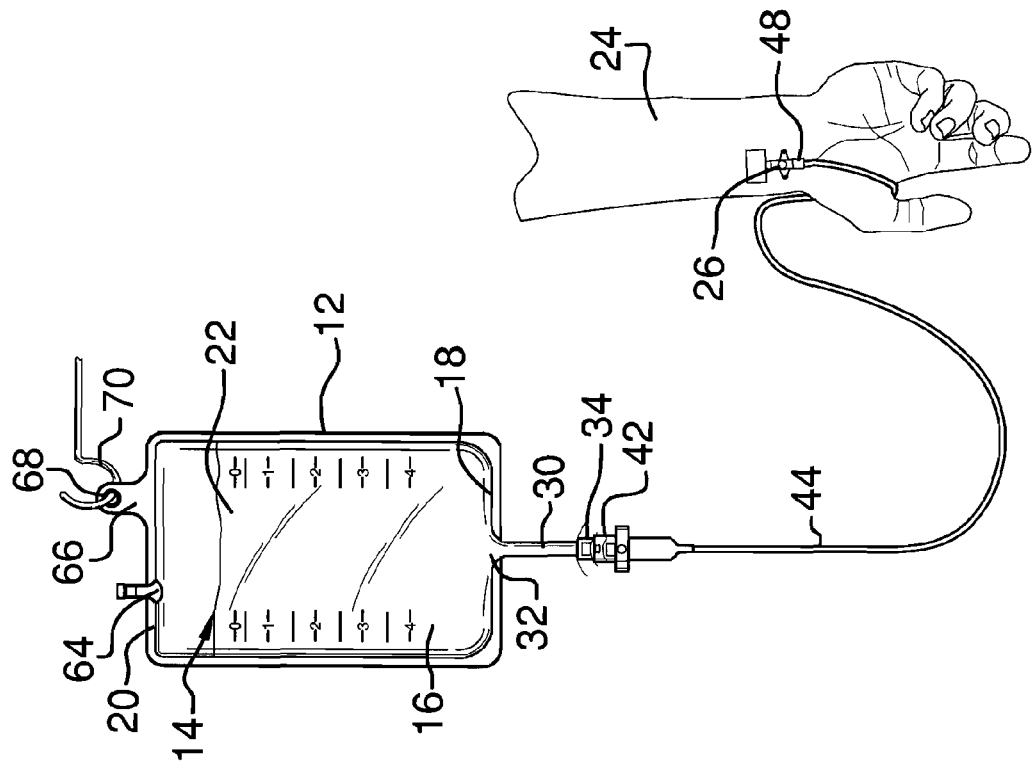
FIG. 6 is a front view of an embodiment of the disclosure in use.
Figure 5:
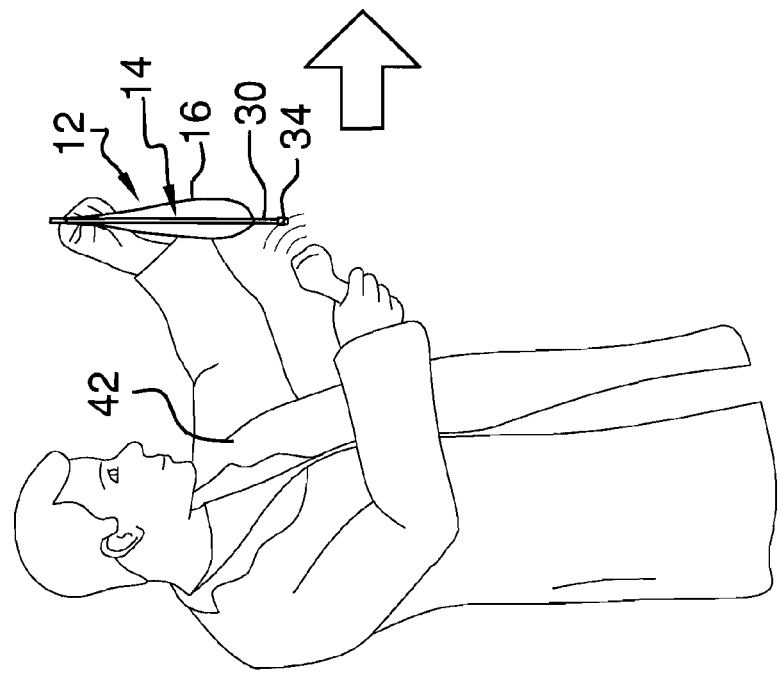
FIG. 5 is a side view of an embodiment of the disclosure in use.
Figure 7:
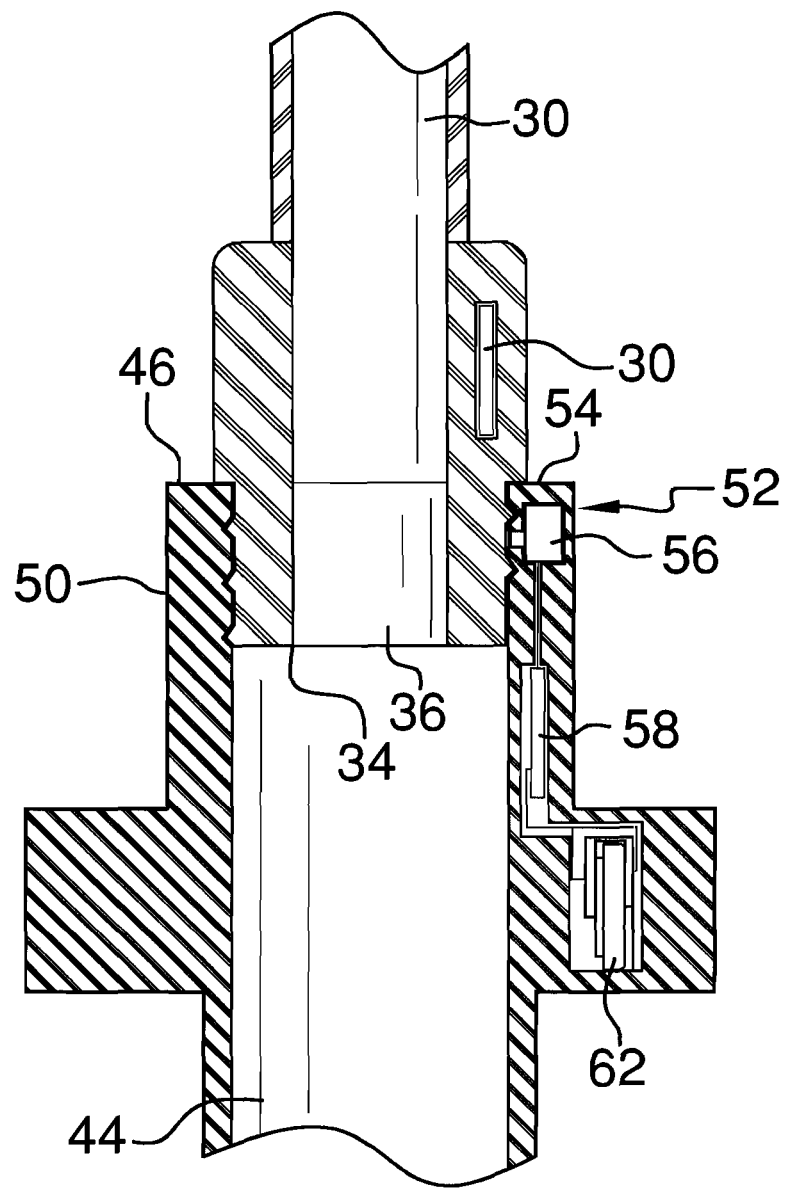
FIG. 7 is a cross-sectional view of an embodiment of the disclosure taken along line 7-7 of FIG. 6.

With reference now to the drawings, and in particular to FIGS. 1 through 7 thereof, a new medication delivery device embodying the principles and concepts of an embodiment of the disclosure and generally designated by the reference numeral 10 will be described.

As best illustrated in FIGS. 1 through 7, the intravenous medication delivery safety assembly 10 generally comprises a transparent bag 12 which has an interior space 14 defined by a perimeter wall 16. The perimeter wall 16 extends between a sealed bottom 18 of the bag 12 and a sealed top 20 of the bag 12. A medication 22 is contained in the interior space 14 of the bag 12. The medication 22 may be prepared for intravenous delivery to a patient 24 through a cannula 26. An inlet opening 64 may be positioned in the sealed top 20 of the bag 12. A tab 66 may extend from the sealed top 20. An aperture 68 is positioned in the tab 66 whereby the bag 12 is configured for being hung from a hanger 70. Indicia 72 may be positioned on the bag 12. The indicia 72 may be spaced in regular intervals to indicate a level of medication 22 remaining within the interior space 14 of the bag 12.

An outlet opening 28 is positioned in the sealed bottom 18 of the bag 12. The outlet opening 28 is in fluid communication with the interior space 14 to facilitate dispensing the medication 22 from the bag 12. A tube 30 has a first end 32 and a second end 34. The first end 32 is coupled to and in fluid communication with the outlet opening 28. Either the first end 32 of the tube 30 or the outlet opening 28 may be flared to promote full draining of the medication 22 from the bag 12. The second end 34 of the tube 30 is more particularly a threaded male end 36.

A microchip 38 is coupled to the tube 30 proximate the second end 34 of the tube 30. The microchip 38 has identifying data 40 corresponding to the medication 22 in the bag 12 prescribed to the patient 24. The identifying data 40 may be wirelessly transmitted and written to the microchip 38 by a pharmaceutical technician 42 or pharmacist preparing the medication 22. The identifying data 40 may include specific information relating exclusively to the specific medication 22, such as concentration, or may provide matched information including the medication name and an identifier specific to the intended patient 24.

A conduit 44 has a first end 46 and a second end 48. The first end 46 of the conduit 44 is selectively coupled to the second end 34 of the tube 30 such that the tube 30 is in fluid communication with the conduit 44. The first end 46 of the conduit 44 is more particularly a threaded female receiver 50. The male end 36 of the tube 30 is complimentary to the female receiver 50 of the conduit 44. The second end 48 of the conduit 44 is configured for coupling to the cannula 26.

A security mechanism 52 is coupled to the conduit 44. The security mechanism 52 selectively prevents coupling of the second end 34 of the tube 30 to the first end 46 of the conduit 44. The security mechanism 52 may provide a physical obstruction to prevent improper or accidental coupling between the tube 30 and the conduit 44. The security mechanism has a pin 54 coupled to a main housing 56 positioned adjacent the female receiver 50. The pin 54 is selectively extendable from the main housing 56 into the female receiver 50 whereby the male end 36 is prevented from being inserted into the female receiver 50. The pin 54 is also selectively retractable into the main housing 56 to permit insertion of the male end 36 into the female receiver 50 whereby the medication 22 may be delivered to the patient 24 through the conduit 44.

A processor 58 is coupled to the conduit 44. The processor 58 has stored confirmation data 60 corresponding to the patient 24 to receive the medication 22. The processor 58 reads the microchip 38 when the microchip 38 is within a pre-determined distance from the processor 58. The processor 58 is operationally coupled to the security mechanism 52 for permitting coupling of the second end 34 of the tube 30 to the first end 46 of the conduit 44 only when the confirmation data 60 corresponds to the identifying data 40. Thus, the possibility of attaching and dispensing an incorrect dosage or even a completely different and potentially harmful medication is greatly reduced. A battery 62 may be coupled to the conduit 44 and electrically coupled to the processor 58 and the security mechanism 52.

In use, the pin 54 extends into the female receiver 50 preventing insertion of the male end 36 until the processor 58 confirms that the identifying data 40 on the microchip 38 corresponds to the appropriate patient 24 to which the conduit 24 and cannula 26 are attached. Upon detection and confirmation of the proper match of medication 22 and patient 24, the pin 54 retracts to permit insertion of the male end 36 into the female receiver 50 to deliver the medication 22 to the patient 24.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. An intravenous medication delivery assembly comprising:
   a bag having an interior space defined by a perimeter wall extending between a sealed bottom of said bag and a sealed top of said bag;
   a medication contained in said interior space of said bag;
   an outlet opening positioned in said sealed bottom of said bag, said outlet opening being in fluid communication with said interior space;
   a tube having a first end and a second end, said first end of said tube being coupled to and in fluid communication with said outlet opening;
   a microchip coupled to said tube proximate said second end of said tube, said microchip having identifying data corresponding to said medication in said bag;
   a conduit having a first end and a second end, the first end of said conduit being selectively coupled to said second end of said tube such that said tube is in fluid communication with said conduit, said second end being configured for coupling to a cannula;
   a security mechanism coupled to said conduit, said security mechanism selectively preventing coupling of said second end of said tube to said first end of said conduit; and
   a processor coupled to said conduit, said processor having confirmation data corresponding to a patient to receive said medication, said processor reading said microchip when said microchip is within a pre-determined distance from said processor, said processor being operationally coupled to said security mechanism for permitting coupling of said second end of said tube to said first end of said conduit when said confirmation data corresponds to said identifying data; and wherein the security mechanism comprises
   a pin that extends into a female receiver for preventing insertion of a male end until the processor confirms that the identifying data on the microchip corresponds to the conduit and cannula attached to the patient; and upon detection and confirmation of the proper match of medication and patient, the pin retracts to permit insertion of the male end into the female receiver to deliver the medication to the patient.

2. The assembly of claim 1, further comprising: said second end of said tube being the male end; and said first end of said conduit being the female receiver, said male end being complimentary to said female receiver.

3. The assembly of claim 2, further including said male end and said female receiver each being threaded.

4. The assembly of claim 2, wherein the pin of said security mechanism is coupled to a main housing positioned adjacent said female receiver, said pin being selectively extendable from said main housing into said female receiver whereby said male end is prevented from being inserted into said female receiver, said pin being selectively retractable into said main housing whereby said male end is insertable into said female receiver.

5. The assembly of claim 4, further including a battery coupled to said conduit, said battery being electrically coupled to said processor and said security mechanism.

6. The assembly of claim 1, further including said bag being transparent.

7. The assembly of claim 1, further including an inlet opening positioned in said sealed top of said bag.

8. The assembly of claim 7, further comprising:
   a tab extending from said sealed top; and
   an aperture positioned in said tab whereby said bag is configured for being hung from a hanger.

9. The assembly of claim 1, further including indicia positioned on said bag, said indicia being spaced to indicate a level of medication remaining within said interior space of said bag.

10. An intravenous medication delivery assembly comprising: a transparent bag having an interior space defined by a perimeter wall, said
   perimeter wall extending between a sealed bottom of said bag and a sealed top of said bag; a medication contained in said interior space of said bag; an outlet opening positioned in said sealed bottom of said bag, said outlet opening being in fluid communication with said interior space;
   a tube having a first end and a second end, said first end of said tube being coupled to and in fluid communication with said outlet opening, said second end of said tube being a threaded male end;
   a microchip coupled to said tube proximate said second end of said tube, said microchip having identifying data corresponding to said medication in said bag;
   a conduit having a first end and a second end, the first end of said conduit being selectively coupled to said second end of said tube such that said tube is in fluid communication with said conduit, said first end of said conduit being a threaded female receiver, said male end of said tube being complimentary to said female receiver of said conduit, said second end of said conduit being configured for coupling to a cannula;
   a security mechanism coupled to said conduit, said security mechanism selectively preventing coupling of said second end of said tube to said first end of said conduit, said security mechanism having a pin coupled to a main housing positioned adjacent said female receiver, said pin being selectively extendable from said main housing into said female receiver whereby said male end is prevented from being inserted into said female receiver, said pin being selectively retractable into said main housing whereby said male end is insertable into said female receiver;

a processor coupled to said conduit, said processor having confirmation data corresponding to a patient to receive said medication, said processor reading said microchip when said microchip is within a pre-determined distance from said processor, said processor being operationally coupled to said security mechanism for permitting coupling of said second end of said tube to said first end of said conduit when said confirmation data corresponds to said identifying data;

and wherein the pin extends into the female receiver for preventing insertion of the male end until the processor confirms that the identifying data on the microchip corresponds to the conduit and cannula attached to the patient; and upon detection and confirmation of the proper match of medication and patient, the in retracts to permit insertion of the male end into the female receiver to deliver the medication to the patient;

a battery coupled to said conduit, said battery being electrically coupled to said processor and said security mechanism;

an inlet opening positioned in said sealed top of said bag; a tab extending from said sealed top; an aperture positioned in said tab whereby said bag is configured for being hung from a hanger; and indicia positioned on said bag, said indicia being spaced to indicate a level of medication remaining within said interior space of said bag.

* * * * *